US010893877B2

(12) United States Patent
Sander et al.

(10) Patent No.: US 10,893,877 B2
(45) Date of Patent: Jan. 19, 2021

(54) GUIDED PUNCH FOR TALAR AUGMENTS

(71) Applicant: Wright Medical Techonology, Inc., Memphis, TN (US)

(72) Inventors: Elizabeth J. Sander, Memphis, TN (US); Robert M. Howles, Bartlett, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 237 days.

(21) Appl. No.: 16/211,983

(22) Filed: Dec. 6, 2018

(65) Prior Publication Data
US 2019/0105063 A1 Apr. 11, 2019

Related U.S. Application Data

(63) Continuation of application No. 14/404,818, filed as application No. PCT/US2014/065786 on Nov. 14, 2014, now Pat. No. 10,159,501.

(51) Int. Cl.
| A61B 17/16 | (2006.01) |
| A61B 17/56 | (2006.01) |
| A61B 17/17 | (2006.01) |
| A61B 17/90 | (2006.01) |

(52) U.S. Cl.
CPC ...... *A61B 17/1697* (2013.01); *A61B 17/1604* (2013.01); *A61B 17/1615* (2013.01); *A61B 17/1682* (2013.01); *A61B 17/1796* (2013.01); *A61B 2017/564* (2013.01); *A61B 2017/90* (2013.01)

(58) Field of Classification Search
CPC .......... A61B 2017/564; A61B 17/1604; A61G 15/02

USPC ................. 606/179, 181, 184, 185
See application file for complete search history.

(56) References Cited

U.S. PATENT DOCUMENTS

| 1,837,067 A | 12/1931 | Reiter |
| 2,419,045 A | 4/1947 | Whittaker |
| 2,818,852 A | 1/1956 | Kugler |
| 3,172,204 A | 3/1965 | Frey |
| 3,800,783 A | 4/1974 | Jamshidi |
| 5,282,866 A | 2/1994 | Cohen et al. |

(Continued)

FOREIGN PATENT DOCUMENTS

| EP | 1570816 A1 | 9/2005 |
| WO | 92-13503 A1 | 8/1992 |

(Continued)

OTHER PUBLICATIONS

Written Opinion of the International Searching Authority, issued in connection with International patent application No. PCT/US2014/065786, dated Jul. 15, 2015, 4 pages.

(Continued)

*Primary Examiner* — David W Bates
(74) *Attorney, Agent, or Firm* — Duane Morris LLP

(57) ABSTRACT

A guided punch is disclosed. The guided punch generally comprises a strike cap comprising a strike surface, a punch comprising a distal cutting edge, and a guide rod. The strike cap defines a first cavity therein. The punch defines a second cavity therein in communication with the first cavity. The guide rod is located within the first and second cavities and extends a predetermined distance beyond the distal cutting edge of the punch. The strike cap and the punch are moveable relative to the guide rod.

6 Claims, 7 Drawing Sheets

(56) References Cited

U.S. PATENT DOCUMENTS

| | | |
|---|---|---|
| 5,351,404 A | 10/1994 | Smith |
| 5,437,675 A | 8/1995 | Wilson |
| 5,665,111 A | 9/1997 | Ray et al. |
| 5,690,636 A | 11/1997 | Wildgoose et al. |
| 5,735,855 A | 4/1998 | Bradley |
| 5,882,340 A | 3/1999 | Yoon |
| 5,957,946 A | 9/1999 | Shuler et al. |
| 6,004,326 A | 12/1999 | Castro et al. |
| 6,080,173 A | 6/2000 | Williamson, IV et al. |
| 6,143,012 A | 11/2000 | Gausepohl |
| 6,176,867 B1 | 1/2001 | Wright |
| 6,193,721 B1 | 2/2001 | Michelson |
| 6,689,147 B1 | 2/2004 | Koster et al. |
| 7,497,861 B2 | 3/2009 | Bharadwaj et al. |
| 7,670,342 B2 | 3/2010 | Bharadwaj et al. |
| 8,162,967 B1 | 4/2012 | Kaiser et al. |
| 8,337,498 B2 | 12/2012 | Rasmussen |
| 9,206,577 B2 | 12/2015 | Lusk |
| 2002/0077641 A1 | 6/2002 | Michelson |
| 2005/0043738 A1 | 2/2005 | Ryan |
| 2010/0076438 A1 | 3/2010 | Correia et al. |
| 2012/0226283 A1 | 9/2012 | Meridew et al. |
| 2013/0123930 A1 | 5/2013 | Burt |
| 2013/0144296 A1 | 6/2013 | Yoko et al. |
| 2013/0172891 A1 | 7/2013 | Bake et al. |
| 2014/0081272 A1 | 3/2014 | Smith et al. |
| 2014/0276842 A1 | 9/2014 | Chernosky et al. |
| 2014/0296916 A1 | 10/2014 | McCormack et al. |

FOREIGN PATENT DOCUMENTS

| | | |
|---|---|---|
| WO | 1996/027345 A2 | 9/1996 |
| WO | 1999/012481 A1 | 3/1999 |
| WO | 2002/062235 A2 | 8/2002 |
| WO | 2005/081863 A2 | 9/2005 |
| WO | 2011/008966 A1 | 1/2011 |
| WO | 2013/126416 | 8/2013 |
| WO | 2014131007 A1 | 8/2014 |

OTHER PUBLICATIONS

First Examination Report dated Mar. 3, 2016, for corresponding Australian patent application No. 2014331641, 7 pages.

First Office Action issued in connection with corresponding Japanese patent application No. 2016-544421, dated Jun. 6, 2017, 3 pages.

First Office Action issued in connection with corresponding Chinese patent application No. 201480038476.2, dated Aug. 30, 2017, 7 pages.

GUIDED PUNCH FOR TALAR AUGMENTS

CROSS-REFERENCE TO RELATED APPLICATIONS

This application is a continuation of U.S. patent application Ser. No. 14/404,818, filed Dec. 1, 2014, which is a national phase entry under 35 U.S.C. 371 of International Patent Application PCT/US2014/065786, filed Nov. 14, 2014, the entireties of which are herein incorporated by reference.

FIELD OF THE INVENTION

The present disclosure is generally related to osteopathic surgery. More specifically, the present disclosure is related to talar augmentation.

BACKGROUND

Some surgical procedures utilize implants having a stem or other protrusion for anchoring the implant to a bone. For example, in total ankle replacement, a talar dome may have a stem extending from a bottom surface into the talas. The stem is configured to maintain the implant in a predetermined orientation with respect to the bone and provide additional fixation into the talus. In order to attach the implant, a hole must be formed in the bone to receive the implant.

Formation of the hole by, for example, a drill, may result in an uneven hole. Current formation techniques do not allow for the formation of holes having non-circular shapes such as, for example, square holes, to receive implants and/or stems.

SUMMARY

In various embodiments, a guided punch is disclosed. The guided punch generally comprises a strike cap comprising a strike surface, a punch comprising a distal cutting edge, and a guide rod. The strike cap defines a first cavity therein. The punch defines a second cavity therein. The second cavity is in communication with the first cavity. The guide rod is located within the first and second cavities and extends a predetermined distance beyond the distal cutting edge of the punch. The strike cap and the punch are moveable relative to the guide rod.

In various embodiments, a method for reaming a hole is disclosed. The method generally comprises forming a pilot hole in a bone, inserting a guide rod of a guided punch into the pilot hole and reaming the pilot hole to a uniform hole using the guided punch. The guided punch comprises a strike cap, a punch coupled to a distal end of the strike cap and having a distal cutting edge. The guide rod extends a predetermined distance beyond the distal cutting edge of the punch. The strike cap and the punch are moveable relative to the guide rod.

In various embodiments, a surgical system is disclosed. The surgical system generally comprises a guided punch assembly, a first punch, and a second punch. The guide punch assembly comprises a strike cap comprising a strike surface. The strike cap defines a first cavity therein. A guide rod is located within the first cavity and extends a predetermined distance beyond a distal edge of the strike cap. A spring is disposed between the guide rod and a surface of the first cavity. The spring is configured to exert a proximal biasing force on the strike cap. The first punch is configured to couple to the strike cap and comprises a first size, a first shape, and a first depth. The second punch is configured to couple to the strike cap and comprises a second size, a second shape, and a second depth.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
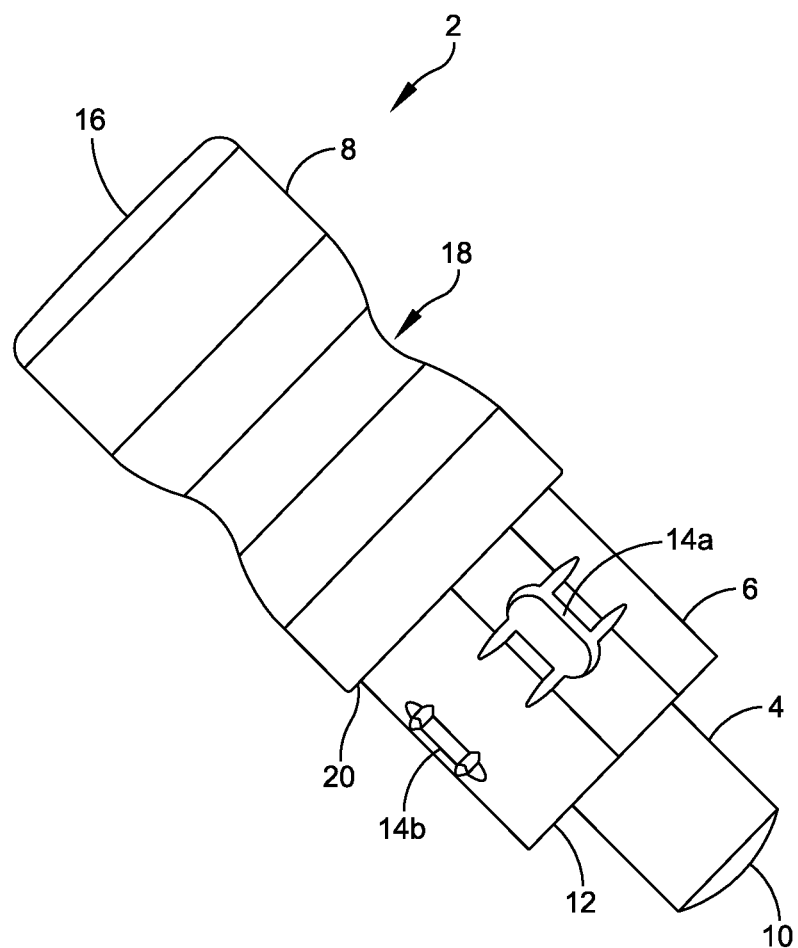
FIG. 1 illustrates a guided punch assembly.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides a guided punch assembly configured for preparing a bone for insertion of an implant, such as, for example, a talar augment. The various embodiments of the guided punch assembly disclosed herein generally comprise a guide pin having a punch slideably positioned about a portion of the guide pin. A strike cap is coupled to the punch. The strike cap and the punch are slideably moveable along a longitudinal length of the guide pin. The punch is configured to ream a hole in a bone, such as, for example, a talas.

FIG. 1 illustrates a guided punch assembly 2. The guided punch assembly 2 comprises a guide pin 4. The guide pin 4 may comprise any suitable shape, such as, for example, a cylinder. The guide pin 4 is sized and configured to fit within a pilot hole formed by a drill in a bone, such as, for example, a talas. In some embodiments, the guide pin 4 comprises a hollow cavity for receiving a spring therein (see FIG. 7). The guide pin 4 comprises a distal tip 10 configured to contact a bottom surface of the pilot hole. In some embodiments, the distal tip 10 comprises a nub configured to be received within a k-wire hole to center the punch assembly 2 in the pilot hole.

The guide punch assembly 2 further comprises a punch 6. The punch 6 comprises an internal cavity or channel (not shown) for receiving the guide pin 4 therein. The punch 6 is concentrically located about a portion of the guide pin 4. The punch 6 is configured to ream a bone section to receive an implant and/or augment. The distal edge of the punch 6 comprises a reaming edge 12 configured to ream a bone. When the punch 6 is driven distally, the reaming edge 12 reams a hole sized and configured to receive the implant. One or more openings 14a, 14b are formed about the periphery of the punch 6 to allow for evacuation of bone matter during reaming and for indication of reaming depth. The punch 6 is movable with respect to the guide pin 4. For example, in the illustrated embodiment, the punch 6 is slideably moveable in a proximal/distal direction over the guide pin 4 such that the punch 6 is moveable along a longitudinal axis of the guide pin 4 while the guide pin 4 remains stationary. The punch 6 may comprise any suitable cross-sectional shape, such as, for example, square, circular, hexagonal, and/or any other suitable shape. In some embodiments, the cross-sectional shape of the punch 6 corresponds to a cross-sectional shape of an implant to be received within the reamed hole.

A strike cap 8 is fixedly coupled to a proximal side of the punch 6. The strike cap 8 is configured to drive the reaming edge 12 of the punch 6 into a bone. The strike cap 8 comprises a strike surface 16. The strike surface 16 provides a flat surface configured to be struck by an instrument, such as a hammer, to exert sufficient force on the punch 6 to drive the reaming edge 12 to a predetermined depth within the bone. The strike cap 8 may also comprise a gripping section 18. The gripping section 18 may comprise, for example, an inset or concave surface configured to provide a firm grip to a clinician and/or a gripping tool. The strike cap 8 may be coupled to the punch 6 by any suitable connection, such as, for example, a threaded connection, a welded connection, a press-fit connection, and/or any other suitable connection. In some embodiments, the punch 6 is selectively separable from the strike cap 8. For example, in some embodiments, the punch 6 comprises a first interchangeable punch coupled to the strike cap 8 by a plurality of threads. The first interchangeable punch may be removed from the strike cap 8 and replaced by a second interchangeable punch having, for example, a different size, shape, and/or predetermined depth. It will be recognized that any number of interchangeable punches having various sizes, shapes, depths, and/or other parameters may be selectively coupled to the guide punch assembly 2.

In operation, the guided punch assembly 2 is positioned at a treatment site by inserting the guide pin 4 into a pilot hole and the reaming edge 12 is driven into a bone section by striking the strike surface 16 of the strike cap 8 with sufficient force, for example, by using a hammer. The strike cap 8 may comprise a lip 20 configured to prevent the punch 6 from extending into a bone beyond a predetermined depth. The lip 20 contacts the bone outside of the reamed hole and prevents further driving of the punch 6 beyond a predetermined depth. In some embodiments, a spring (see FIG. 7) is located within an internal cavity of the guide pine 4 to bias the punch 6 and the strike cap 8 in a proximal direction. When the strike cap 8 is struck, the strike cap 8 and the punch 6 are driven distally to the predetermined depth defined by the lip 20. The spring is compressed and exerts a proximal force to return the punch 6 and the strike cap 8 to a proximal-most (or initial) position.

Figure 2:
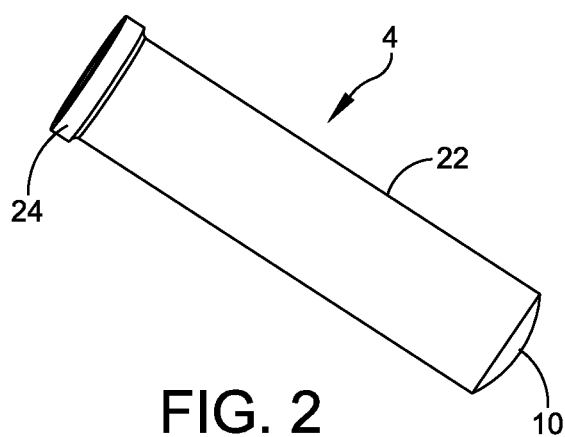
FIG. 2. illustrates a guide pin of the guided punch assembly of FIG. 1.

FIG. 2 illustrates one embodiment of a guide pin 4. The guide pin 4 comprises a shaft 22 having a distal tip 10 and a proximal lip 24. The shaft 22 and the distal tip 10 are sized and configured to be received within a pre-drilled pilot hole. The shaft 22 extends a predetermined length along a longitudinal axis. The length of the shaft 22 corresponds to the depth of the hole to be reamed in the bone and the length of the strike cap 8. For example, in some embodiments, the length of the shaft 22 is configured to extend from the strike surface 16 of the strike cap 8 to the reaming edge 12 of the punch 6. The distal tip 10 is configured to contact the bottom of the pilot hole and may comprise a nub (see FIG. 7) configured to interface with a k-wire hole to center the guide pin 4 in the pilot hole. A proximal lip 24 is located at the proximal end of the guide pin 4. The proximal lip 24 comprises a section having a wider diameter than the shaft. In some embodiments, the proximal lip 24 is configured to support a spring located within an inner cavity defined by the strike cap 8 and/or is configured to maintain the guide pin 4 within the punch 6 and strike cap 8 when the punch assembly 2 is fully assembled. In some embodiments, the guide pin 4 defines a cavity configured to receive a spring therein. The cavity is defined by an opening on the proximal end of the guide pin 4 and extends at least partially into the shaft 22.

Figure 3:
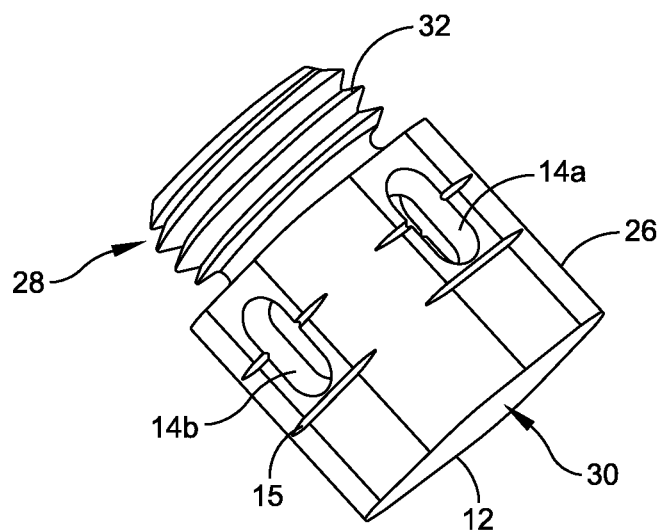
FIG. 3 illustrates a punch of the guided punch assembly of FIG. 1.

FIG. 3 illustrates one embodiment of a punch 6. The punch 6 comprises a reaming section 26 and a coupling section 28. The reaming section 26 is sized and configured to ream a hole into a bone. The reaming section 26 defines a distal reaming edge 12. A distal opening 30 is configured to receive a bone section during reaming. The coupling section 28 is configured to couple the punch 6 to a strike cap 8. In the illustrated embodiment, the coupling section 28 comprises a plurality of threads, although it will be recognized that any suitable coupling feature may be used. A channel extends through the coupling section 28 and the distal opening 30 to allow the punch 6 to slide over the guide pin 4. The punch 6 may comprise any suitable material, such as, for example, stainless steel.

Figure 4:
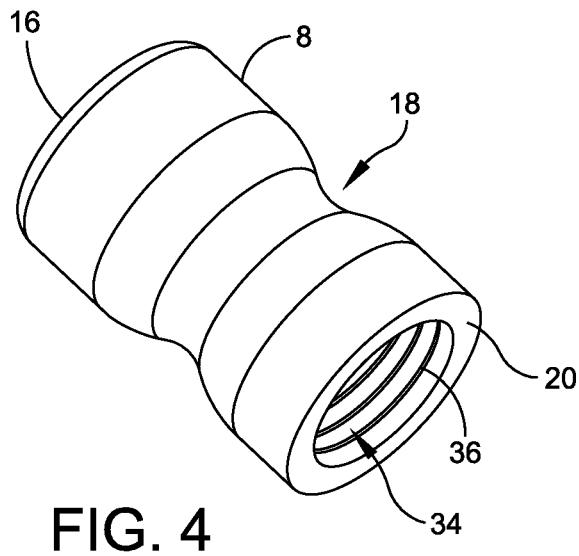
FIG. 4 illustrates a strike cap of the guided punch assembly of FIG. 1.

FIG. 4 illustrates one embodiment of a strike cap 8. The strike cap 8 comprises an internal cavity 34 having a distal opening configured to receive the coupling section 28 and the guide pin 4 therein. The distal opening may comprise one or more mating features to couple the strike cap 8 to the punch 6. For example, in the illustrated embodiment, the distal opening 35 of the strike cap 8 comprises an internal threading 36 configured to couple to the external threads 32 of the punch 6 (see FIG. 3). In some embodiments, the strike cap 8 is detachable from the punch 6 to allow two or more interchangeable punches to be used with the strike cap 8. The distal end of the strike cap 8 further defines a lip 20. The lip 20 is configured to prevent a punch 6 coupled to the strike cap 8 from being driven beyond a predetermined depth into a bone section. The strike cap 8 may be configured to receive a spring within the internal cavity 34 to provide a proximal bias to the strike cap 8 and the punch 6 with respect to the guide pin 4 when the punch assembly 2 is fully assembled.

Figure 5:
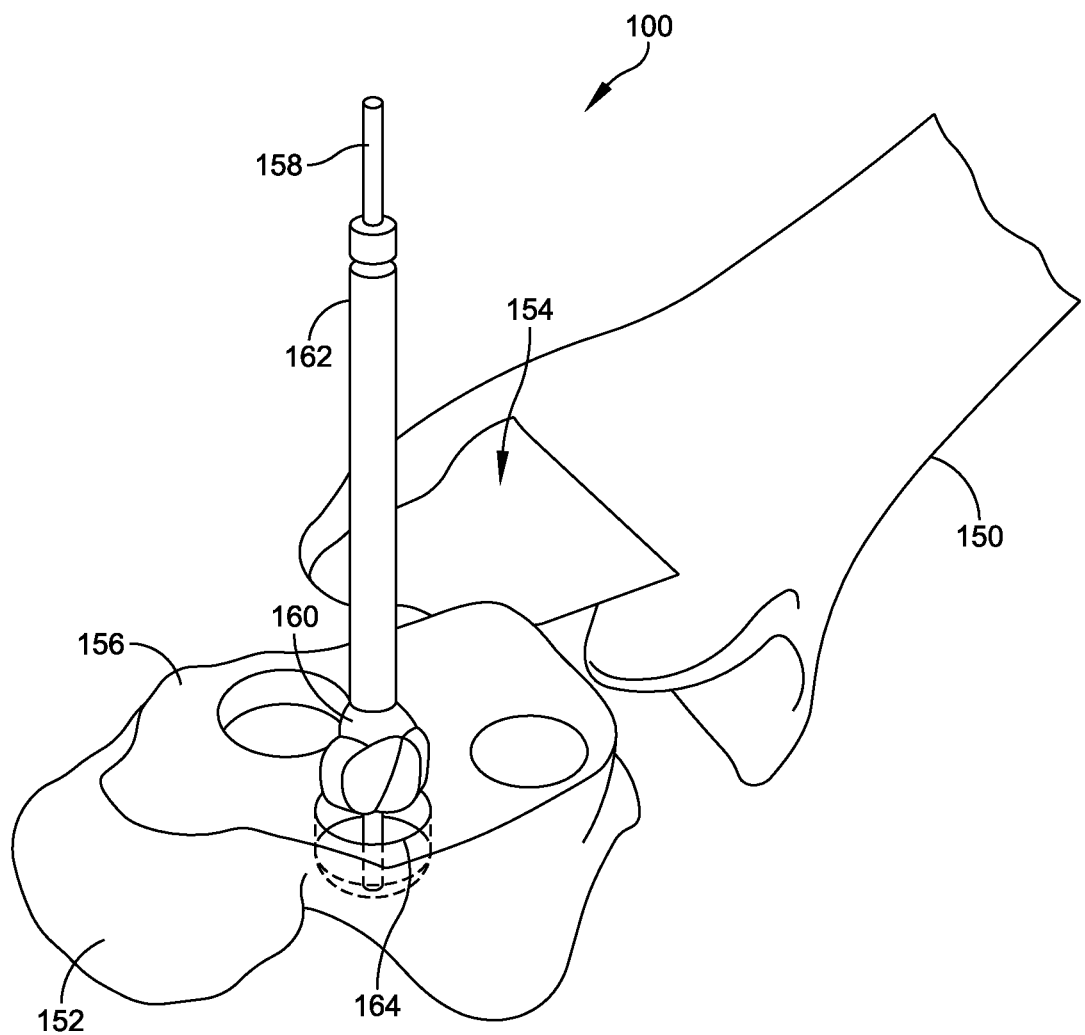
FIG. 5 illustrates formation of a pilot hole in a bone.

FIGS. 5-8 illustrate various stages of forming a hole in a bone 152 of a joint 100 using a guided punch assembly 102. FIG. 9 is a flowchart illustrating one embodiments of a method 200 of forming the hole in a bone. FIG. 5 illustrates a first bone 150 and a second bone 152. The first bone 150 has a resected section 154. The second bone 152 comprises a resected section 156. In a first step 202, a k-wire 158 is inserted through a portion of the second bone 152. The k-wire 158 acts as a guide for a drill 160. In a second step 204, the drill 160 inserted over the k-wire 158 and rotated via shaft 162 to form a pilot hole 164 in the second bone 152. The pilot hole 164 comprises a first diameter. The drill 160 and the k-wire 158 are removed after forming the pilot hole 164.

Figure 6:
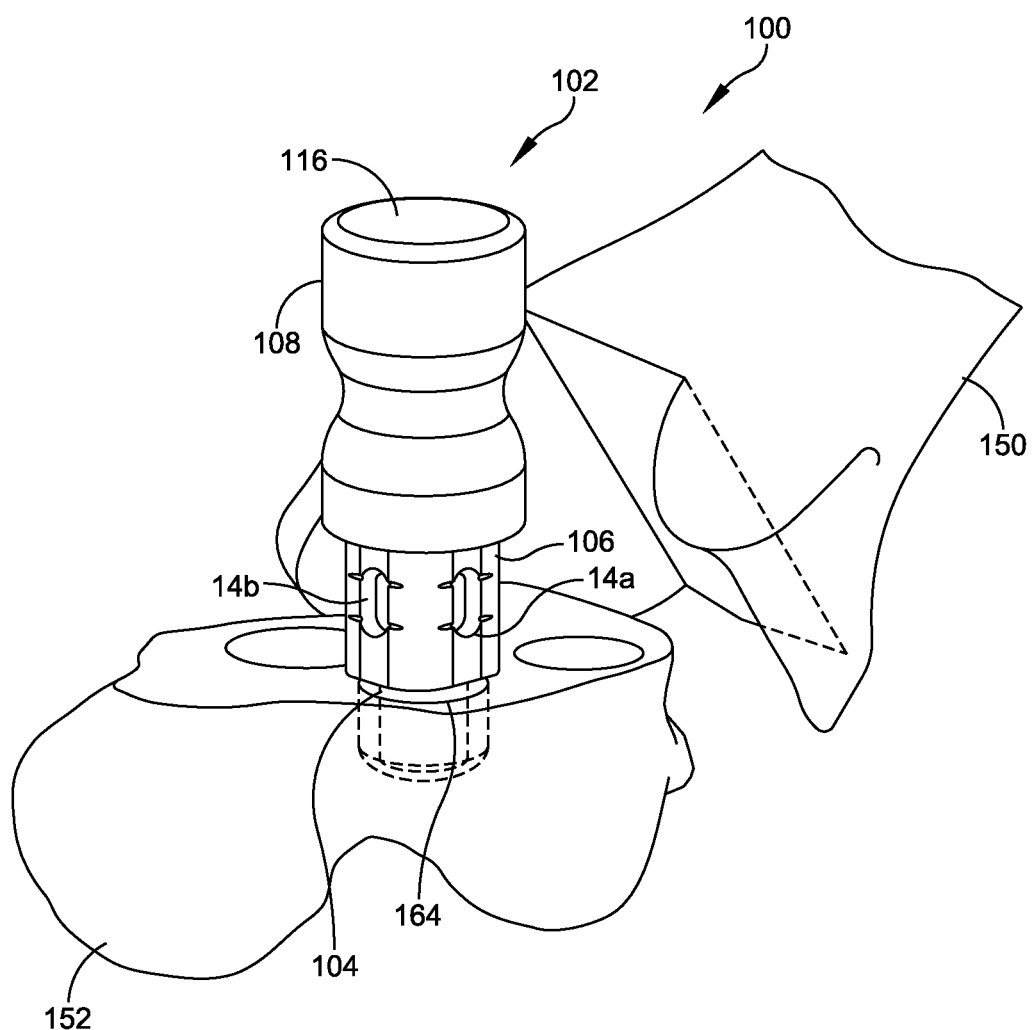
FIG. 6 illustrates a guided punch assembly located within a pilot hole formed in the bone.
Figure 7:
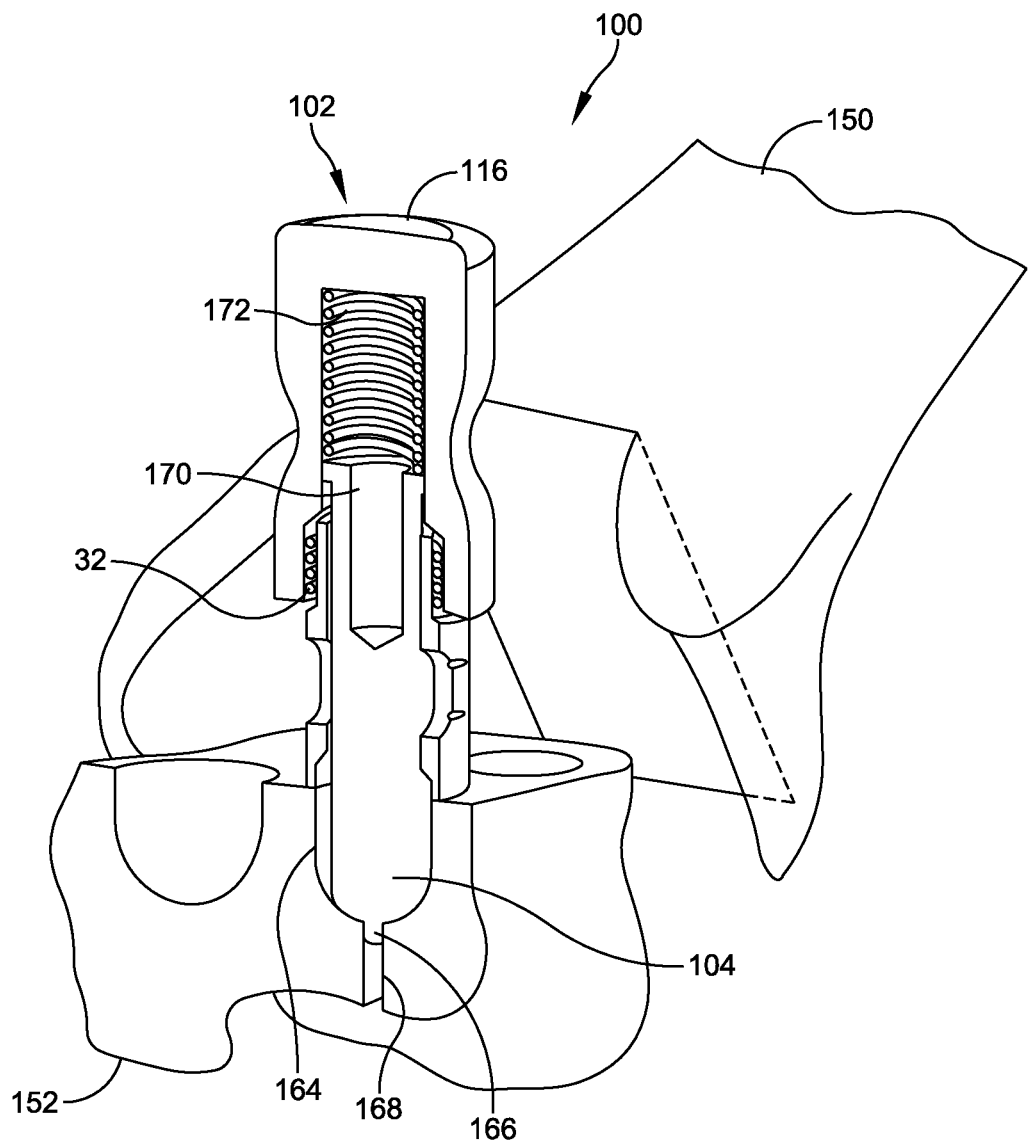
FIG. 7 illustrates a cross-sectional view of the guided punch assembly of FIG. 6 in initial position.

After forming the pilot hole 164, a punch assembly 102 is positioned at the treatment site in a third step 206. FIG. 6 illustrates the punch assembly 102 in an initial position. The guide pin 104 of the punch assembly 102 is inserted into the pilot hole 164 formed in the second bone 152. In various embodiments, the diameter of the guide pin 104 may be equal to or smaller than the diameter of the pilot hole 164. FIG. 7 illustrates a cross-sectional view of the second bone 152 and the punch assembly 102. As shown in FIG. 7, the guide pin 104 is positioned within the pilot hole 164. A nub 166 may be coupled to the distal tip of the guide pin 104. The nub 166 is sized and configured to fit within a hole 168 left by the k-wire 158. The nub 166 centers the guide pin 104 within the pilot hole 164. In some embodiments, the guide pin 104 comprises a length such that the cutting edge 112 of the punch 106 rests against the second bone 152 when the guide pin 104 is inserted into the pilot hole 164. The punch 106 is coupled to a strike cap 108 by a threaded connection 32.

Figure 8:
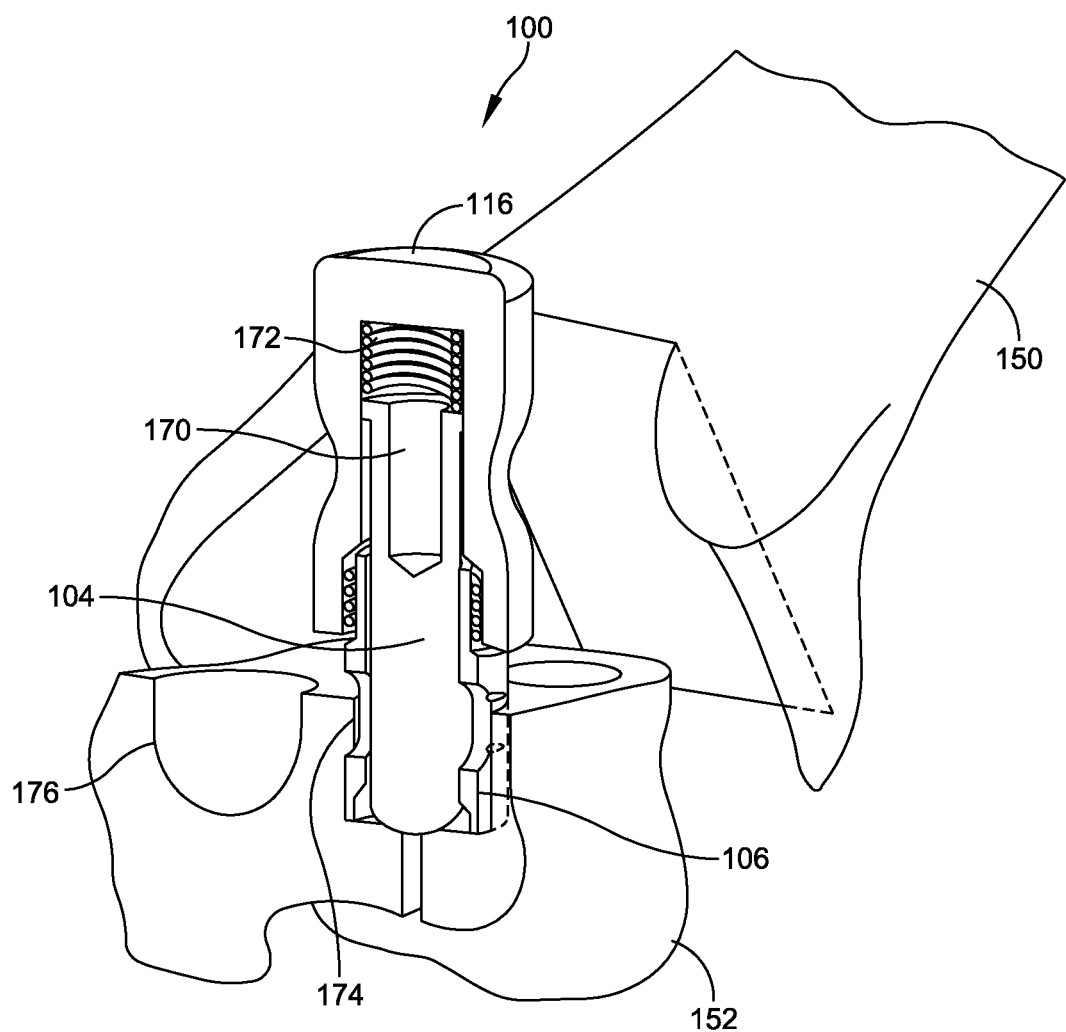
FIG. 8 illustrates a cross-sectional view of the guided punch assembly of FIG. 6 in a punched position.
Figure 9:
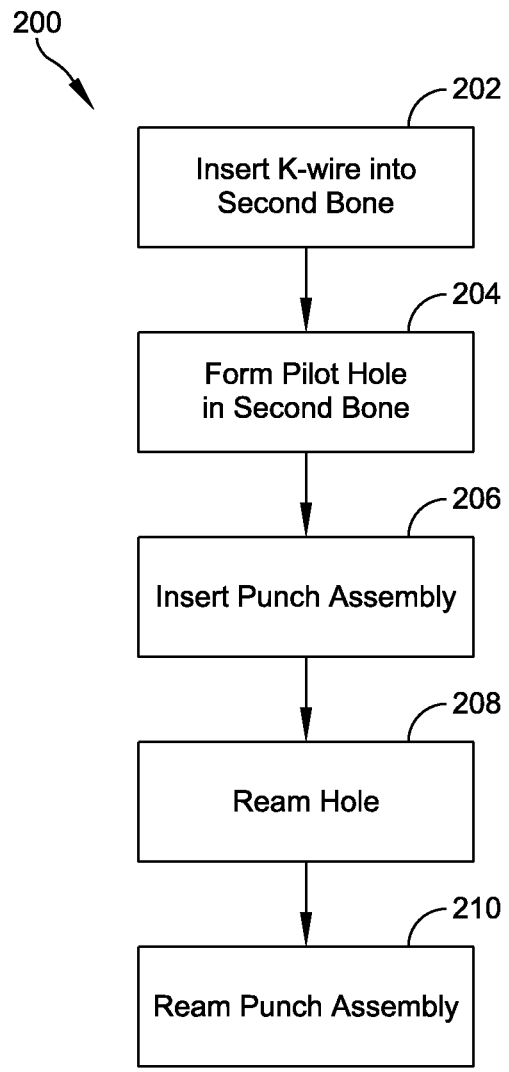
FIG. 9 is a flowchart illustrating one embodiment of a method of reaming a hole in a bone.

In a fourth step 208, once the punch assembly 102 is positioned in the pilot hole 164, the strike surface 116 of the strike cap 108 is struck by, for example, a hammer, to drive the punch 106 to a distal-most position as shown in FIG. 8. The punch 106 is driven into the second bone 152 by the strike cap 108. The punch 106 removes a bone section to ream a uniform hole 174 in the second bone 152. The punch 106 and the strike cap 108 move relative to the guide pin 104, which remains stationary. A spring 172 located within the strike cap 108 is compressed. In some embodiments, the spring 172 is located within a spring recess 170 formed in the guide pin 104. The spring 172 drives the strike cap 108 and the punch 106 proximally after the reamed hole 174 is formed. The reamed hole 174 comprises a uniform hole having a size and shape matching the size and shape of the punch 106. In a fifth step 210, the punch assembly 102 is removed from the reamed hole 174 and an implant is inserted therein (not shown). In some embodiments, the punch 106 comprises a first punch having a first size, a first shape, and a first depth. The first punch may be detached from the strike cap 108 by, for example, rotating the external threads of the first punch out of the internal threads of the strike cap 108. A second punch comprising at least one of a second size, a second shape, and/or a second depth may be coupled to strike cap 108. The second punch may be used to ream a second hole having a size, shape, and/or depth different than the first reamed hole 174.

In various embodiments, a guided punch is disclosed. The guided punch generally comprises a strike cap comprising a strike surface, a punch comprising a distal cutting edge, and a guide rod. The strike cap defines a first cavity therein. The punch defines a second cavity therein in communication with the first cavity. The guide rod is located within the first and second cavities and extends a predetermined distance beyond the distal cutting edge of the punch. The strike cap and the punch are moveable relative to the guide rod.

In some embodiments, the guide punch comprises a spring located in the first cavity and configured to bias the strike cap and the punch to a proximal-most position.

In some embodiments, the punch comprises one or more holes configured to receive bone material therein.

In some embodiments, the punch is coupled to the strike cap by a threaded connection.

In some embodiments, the guide rod is sized and configured to be received within a pilot hole formed in a bone.

In some embodiments, the guide rod comprises a nub on a distal end sized and configured to interface with a k-wire hole.

In some embodiment, the bone comprises a talas.

In some embodiments, the strike cap comprises a distal lip sized and configured to prevent the punch from being driven beyond a predetermined depth.

In various embodiments, a method for reaming a hole is disclosed. The method generally comprises forming a pilot hole in a bone, inserting a guide rod of a guided punch into the pilot hole and reaming the pilot hole to a uniform hole using the guided punch. The guided punch comprises a strike cap, a punch coupled to a distal end of the strike cap and having a distal cutting edge. The guide rod extends a predetermined distance beyond the distal cutting edge of the punch. The strike cap and the punch are moveable relative to the guide rod.

In some embodiments, the step of forming the pilot hole comprises inserting a k-wire through the bone, inserting a drill over the k-wire, and rotating a drill head of the drill to form the pilot hole in the bone.

In some embodiments, the step of reaming the pilot hole comprises striking a strike surface of the strike cap to drive the strike cap and the punch distally.

In some embodiments, the step of reaming the pilot hole further comprises compressing, by the strike cap, a spring located within a cavity of the strike cap and returning, by the spring, the strike cap and the punch to a proximal-most position.

In some embodiments, the method further comprises, prior to inserting the guide rod into the pilot hole, a step of assembling the guide punch. Assembling the guide punch comprises: inserting the guide rod into an internal cavity of the strike cap, sliding the punch over the guide rod, and coupling the punch to the strike cap.

In some embodiments, the punch comprises a first punch. The first punch comprises a first depth, a first size, and a first shape. The method further comprises removing the first punch from the strike cap and coupling a second punch to the strike cap. The second punch comprises a second depth, a second size, and a second shape.

In various embodiments, a surgical system is disclosed. The surgical system generally comprises a guided punch assembly, a first punch, and a second punch. The guide punch assembly comprises a strike cap comprising a strike surface. The strike cap defines a first cavity therein. A guide rod is located within the first cavity and extends a predetermined distance beyond a distal edge of the strike cap. A spring is disposed between the guide rod and a surface of the first cavity. The spring is configured to exert a proximal biasing force on the strike cap. The first punch is configured to couple to the strike cap and comprises a first size, a first shape, and a first depth. The second punch is configured to couple to the strike cap and comprises a second size, a second shape, and a second depth.

In some embodiments, the strike cap comprises an internal thread in the first cavity and each of the first and second punches comprise an external thread configured to couple to the internal thread of the strike cap.

In some embodiments, the guide rod is sized and configured to be received within a pilot hole formed in a bone.

In some embodiments, the first size, first shape, and the first depth of the first punch correspond to a first implant.

In some embodiments at least one of the second size, the second shape, and the second depth is different from respective first size, first shape, or first depth.

In some embodiments, the strike cap comprises a distal lip configured to prevent a punch coupled to the strike cap from exceeding a predetermined depth Although the subject matter has been described in terms of exemplary embodiments, it is not limited thereto. Rather, the appended claims should be construed broadly, to include other variants and embodiments, which may be made by those skilled in the art.

What is claimed is:

1. A method for performing surgery comprising:
    providing a device comprising:
        a strike cap comprising a strike surface, wherein the strike cap defines a first cavity therein;
        a punch coupled to a distal end of the strike cap, the punch comprising a distal cutting edge, and wherein the punch defines a second cavity therein in communication with the first cavity;
        a guide rod located within the first and second cavities and extending a predetermined distance beyond the distal cutting edge of the punch, wherein the strike cap and the punch are moveable relative to the guide rod, wherein the guide rod defines a proximal lip configured to interact with a proximal surface of the punch to maintain the guide rod at least partially within the first cavity; and
        a spring positioned proximally of the guide rod within the first cavity, wherein the spring is configured maintain the guide rod in a fixed position with respect to a bone when the strike cap and punch are moved relative to the guide rod in response to an impaction force;
    forming a pilot hole in a bone;
    inserting a guide rod of a guided punch into the pilot hole, wherein the guided punch comprises a strike cap, a punch coupled to a distal end of the strike cap and having a distal cutting edge, wherein the guide rod extends a predetermined distance beyond the distal cutting edge of the punch, and wherein the strike cap and the punch are moveable relative to the guide rod, wherein the guide rod defines a proximal lip configured to interact with a proximal surface of the punch to maintain the guide rod at least partially within the first cavity, and a spring positioned proximally of the guide rod within the first cavity; and
    reaming the pilot hole to a uniform hole using the guided punch, wherein the spring maintains the guide rod in a fixed position with respect to a bone when an impaction force is applied to the strike surface of the strike cap.

2. The method of claim 1, wherein forming the pilot hole comprises:
    inserting a k-wire through the bone; inserting a drill over the k-wire; and
    rotating a drill head of the drill to form the pilot hole in the bone.

3. The method of claim 1, wherein reaming the pilot hole comprises striking a strike surface of the strike cap to drive the strike cap and the punch distally.

4. The method of claim 3, wherein reaming the pilot hole further comprises:
    compressing, by the strike cap, a spring located within a cavity of the strike cap; and
    returning, by the spring, the strike cap and the punch to a proximal-most position.

5. The method of claim 1, further comprising, prior to inserting the guide rod into the pilot hole, a step of assembling the guide punch, wherein assembling the guide punch comprises:
    inserting the guide rod into an internal cavity of the strike cap;
    sliding the punch over the guide rod; and
    coupling the punch to the strike cap.

6. The method of claim 5, wherein the punch comprises a first punch, wherein the first punch comprises a first depth, a first size, and a first shape, wherein the method further comprises:
    removing the first punch from the strike cap; and coupling a second punch to the strike cap, wherein the second punch comprises a second depth, a second size, and a second shape.

* * * * *